US00PP19818P2

(12) United States Plant Patent
Van Den Top

(10) Patent No.: US PP19,818 P2
(45) Date of Patent: Mar. 10, 2009

(54) HOSTA PLANT NAMED 'REGAL SUPREME'

(50) Latin Name: ***Hosta* sp.**
Varietal Denomination: Regal Supreme

(76) Inventor: Hendrik Jan Van Den Top, Wesselseweg 46, Barneveld (NL), 3771 PC ( * ) Notice: Subject to any disclaimer, the term of this patent is extended or adjusted under 35 U.S.C. 154(b) by 0 days.

(21) Appl. No.: 12/011,166

(22) Filed: Jan. 24, 2008

(51) Int. Cl.
*A01H 5/00* (2006.01)

(52) U.S. Cl. ..... Plt./353
(58) Field of Classification Search ..... Plt./353
See application file for complete search history.

*Primary Examiner*—Annette H Para
(74) *Attorney, Agent, or Firm*—Jondle & Associates, P.C.

(57) ABSTRACT

A new Hosta plant particularly distinguished by green, ovate leaves flushed with greyed-green and having a wide, yellow leaf margin, a broad inverted triangle plant shape, moderate to high vigor, and purple to violet flowers is disclosed.

2 Drawing Sheets

Genus and species: *Hosta* sp.
Variety denomination: 'Regal Supreme'.

BACKGROUND OF THE NEW PLANT

The present invention comprises a new and distinct cultivar of *Hosta,* botanically known as *Hosta* sp. and hereinafter referred to by the cultivar name 'Regal Supreme'. The new cultivar originated from a naturally-occurring whole-plant mutation in Barneveld, The Netherlands, of the parent *Hosta* plant 'Krossa Regal' (unpatented).

The new cultivar was found and selected in an outdoor controlled environment in August 2003 from the results of the naturally-occurring whole-plant mutation in Barneveld, The Netherlands. The present invention has been found to retain its distinctive characteristics through successive asexual propagations.

SUMMARY OF THE INVENTION

The following are the most outstanding and distinguishing characteristics of this new cultivar when grown under normal horticultural practices in Barneveld, The Netherlands.

1. Green, ovate leaves flushed with greyed-green and having a wide, yellow leaf margin;
2. A broad inverted triangle plant shape;
3. Moderate to high vigor; and
4. Purple to violet flowers.

DESCRIPTION OF THE PHOTOGRAPHS

This new *Hosta* plant is illustrated by the accompanying photographs which show blooms and foliage of the plant in full color, the colors shown being as true as can be reasonably obtained by conventional photographic procedures. The photographs are of a 1-year-old plant grown outdoors in Bameveld, The Netherlands.

DESCRIPTION OF THE NEW CULTIVAR

Figure 1:
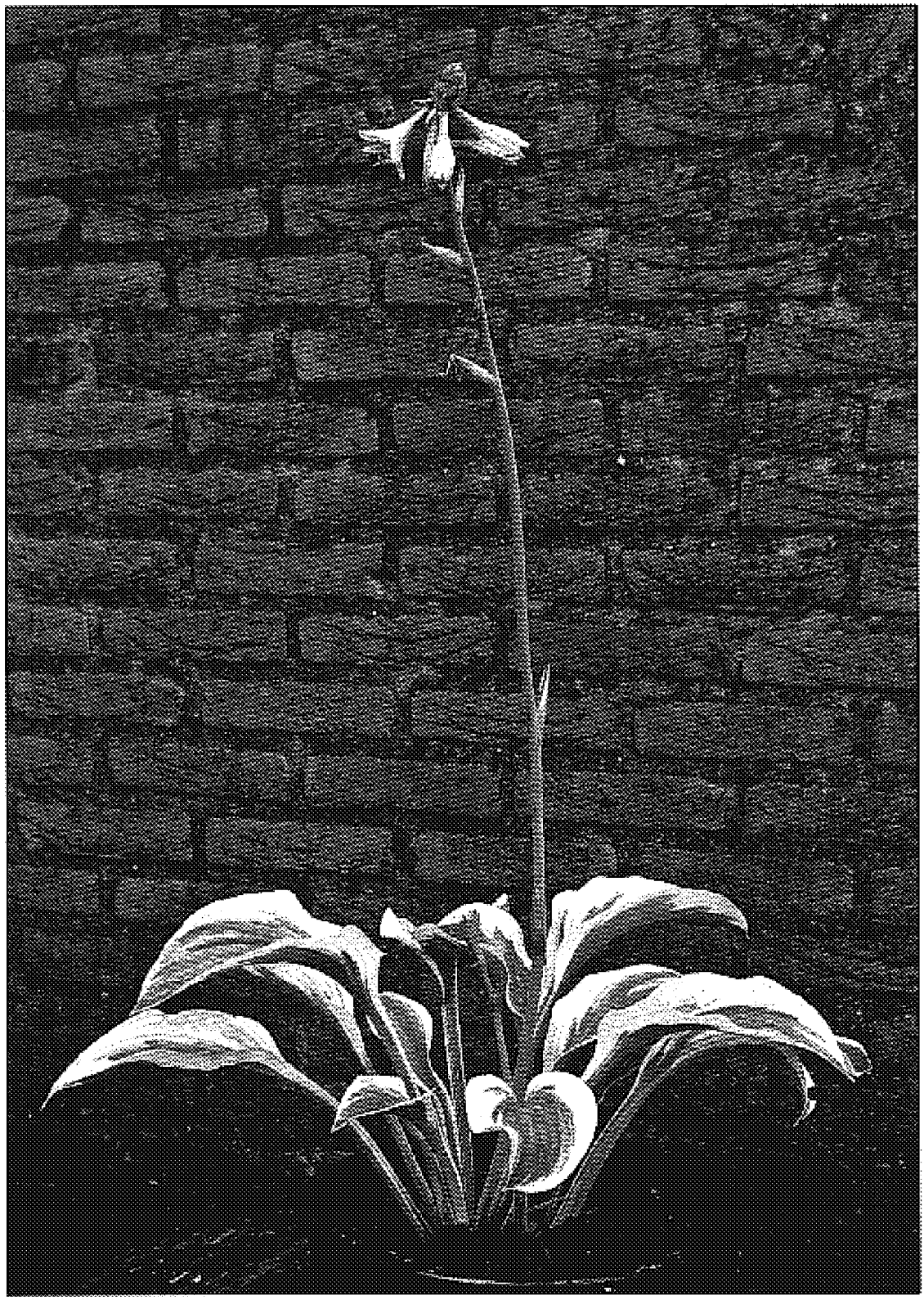
FIG. 1 shows the overall plant habit, including inflorescence and foliage.
Figure 2:
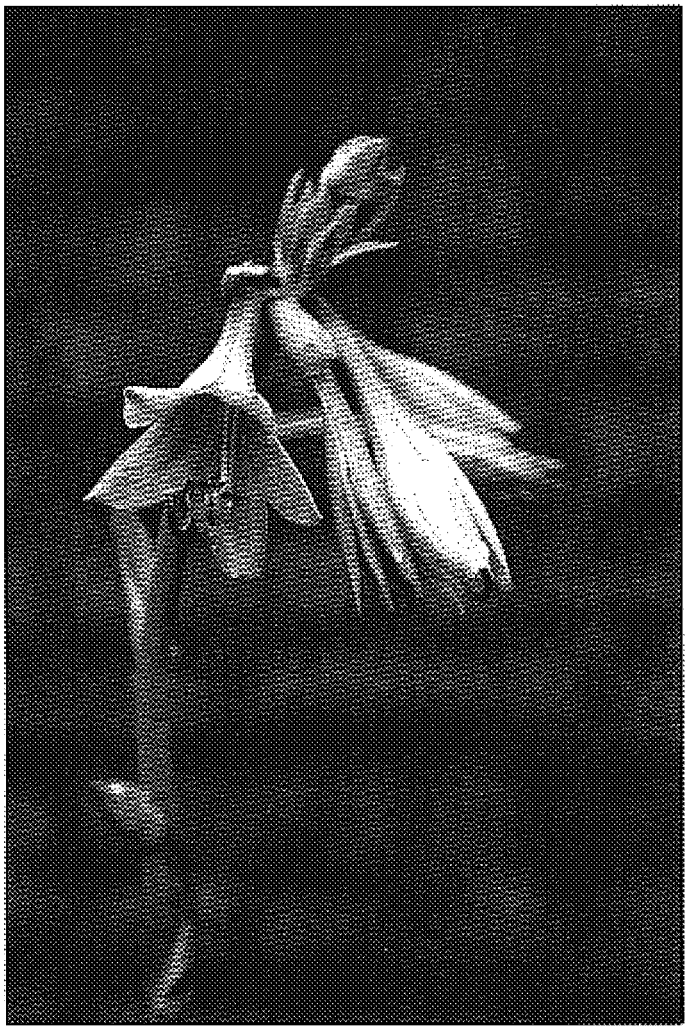
FIG. 2 shows the mature inflorescence of the plant.
Figure 3:
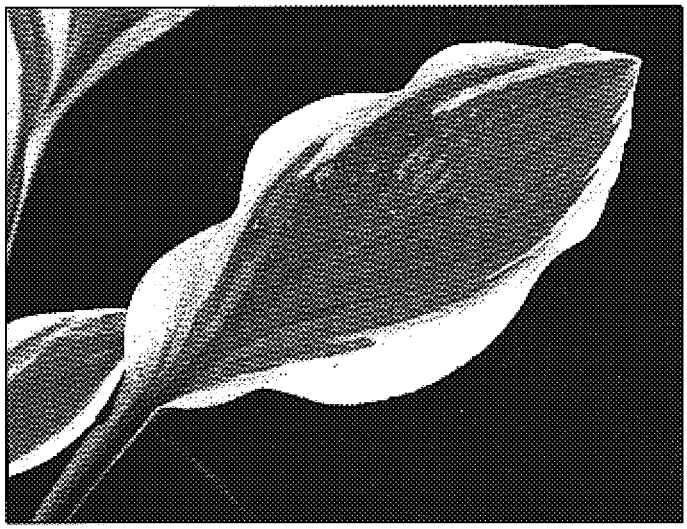
FIG. 3 shows a mature leaf of the plant.

The following detailed description sets forth the distinctive characteristics of 'Regal Supreme'. The data which define these characteristics were collected from asexual reproductions carried out in Barneveld, The Netherlands. The plant history was taken in July on 1-year-old plants grown in 15 liter containers which were planted and grown outdoors in daytime temperatures between 12° C. and 30° C. and nighttime temperatures between 4° C. and 16° C. No pinchings, growth retardants or photoperiodic treatments were used. Observations were made when the plants were in natural outdoor light. Color references are primarily to the R.H.S. Colour Chart of The Royal Horticultural Society of London (R.H.S.) (2001).

DETAILED BOTANICAL DESCRIPTION

Classification:
- *Family.*—Funkiaceae.
- *Botanical.*—*Hosta* sp.
- *Common name.*—Hosta.

Parentage: Naturally occurring whole-plant mutation of 'Krossa Regal' (unpatented).

Plant:
- *Form.*—Herbaceous perennial.
- *Habit and vigor.*—Broad, spreading-upright, inflorescences grow from a basal rosette of leaves; moderate to high vigor.
- *Shape.*—Broad inverted triangle with flowers on top.
- *Height.*—25.5 cm to the top of the foliage; 79.4 cm to the top of the inflorescence.
- *Diameter.*—54.6 cm.
- *Growth rate.*—20.0 cm per month.
- *Flowering response.*—9 months.
- *Flowering habit.*—Continuously from July to September.
- *Time to produce a finished flowering plant.*—20 weeks.
- *High temperature tolerance.*—Tolerant to at least 95° F.
- *Lower temperature tolerance.*—Tolerant to at least −22° F.
- *Roots.*—Crème-white, sparse to moderate, thick, fibrous.

Leaves:
*Arrangement.*—Singe, basal rosette.
*Quantity of leaves (per rosette).*—7.
*Durability to stress.*—Moderate to high.
*Shape.*—Ovate, moderately carinate.
*Apex.*—Apiculate.
*Base.*—Attenuate.
*Margin.*—Entire.
*Color (mature leaves).*—Upper surface: RHS 137B (Green), flushed with RHS 189A (Greyed-green); margin RHS 150D (Yellow) to RHS 4D (Yellow-green) and RHS 8C near the tip. Lower surface: RHS 137A (Green), covered with a thin RHS 188A to RHS 188B (Greyed-green) waxy layer; margin RHS 8D (Yellow).
*Color (immature leaves).*—Upper surface: RHS 137B (Green), flushed with RHS 189A (Greyed-green); margin RHS 150D (Yellow) to RHS 4D (Yellow-green). Lower surface: RHS 137A (Green), covered with a thin RHS 188A to RHS 188B (Greyed-green) waxy layer; margin RHS 8D (Yellow).
*Size.*—Length: 19.0 cm. Width: 10.6 cm.
*Texture.*—Dull, smooth, furrowed on veins.
*Pubescence.*—Absent.
*Venation.*—Pattern: Camptodrome. Color: Upper surface: RHS 137B (Green), margins RHS 6D (Yellow). Lower surface: Main vein RHS 144A to RHS 144B, secondary veins RHS 137A (Green), margins RHS 6D (Yellow).
*Petiole.*—Shape: V-shaped. Length: 17.6 cm. Width: 1.2 cm. Height: 0.9 cm. Color: Upper surface: RHS 137B (Green) striped and margin RHS 150D (Yellow) to RHS 4D (Yellow-green). Lower surface: RHS 144A (Yellow-green) to RHS 144B (Yellow-green) covered with a thin waxy layer RHS 188A (Greyed-green) to RHS 188B (Greyed-green), margin RHS 150D (Yellow) to RHS 4D (Yellow-green).

Flower Buds:
*Color.*—RHS 76A (Purple) to RHS 85A (Violet), at the tip RHS 147B (Yellow-green).
*Shape.*—Oblanceolate
*Size.*—Length: 2.3 cm. Diameter: 0.4 cm.
*Rate of opening.*—Per flowering stem, approximately 5% opens at once, all flowers per inflorescence have opened within approximately 4 weeks.

Inflorescence:
*Blooming habit.*—Continuous from July to September.
*Inflorescence type and arrangement.*—Self cleaning; terminal raceme.
*Natural flowering season.*—Summer to late summer.
*Habit.*—Basal rosette with flowering stem developing from the center.
*Number of stems.*—2.
*Flowering stem.*—Length: 78.8 cm. Diameter: 0.70 cm.
*Height (from lowest flower to top of inflorescence).*—20.1 cm.
*Width.*—9.4 cm.
*Fragrance.*—Absent.
*Flower number (per inflorescence).*—16.
*Quantity of flowers per lateral stem.*—13.
*Quantity of flower buds per lateral stem.*—13.
*Quantity of flower and buds per plant.*—32.
*Flower longevity on plant.*—3 days.

Peduncle:
*Color.*—RHS 137C (Green), covered with a thin waxy layer, RHS 188A (Greyed-green) to RHS 188B (Greyed-green).
*Length.*—59.3 cm.
*Diameter.*—0.7 cm.
*Angle.*—10° (0° is straight upright).
*Strength.*—Strong.

Pedicel:
*Color.*—RHS N187B (Greyed-purple).
*Length.*—0.6 cm.
*Diameter.*—0.2 cm.
*Angle.*—110° (0° is straight on top of the peduncle).
*Strength.*—Strong.

Floral bract:
*Location.*—At the base of each pedicel.
*Number.*—One.
*Shape.*—Ovate, concave.
*Length.*—2.4 cm.
*Width.*—0.17 cm.
*Apex.*—Acute.
*Base.*—Cuneate.
*Color.*—Upper surface: RHS 147B (Yellow-green) to RHS 147C (Yellow-green), margin RHS 159A (Orange-white) to RHS 159B (Orange-white). Lower surface: RHS 144A (Yellow-green), margin RHS 156D (Yellow-green) to RHS 159A (Orange-white) to RHS 159B (Orange-white).

Flowers:
*Type.*—Campanulate.
*Shape.*—Campanulate.
*Aspect.*—Outward, slightly drooping.
*Fragrance.*—Absent.
*Size.*—Height (flower depth): 5.0 cm. Diameter: 3.6 cm.
*Tepals.*—Arrangement: Rotate, fused into campanulate shape, upper ⅓ of the tepals are free. Shape: Oblanceolate. Appearance: Dull, smooth. Number: 6, based fused with the upper 37.5% of tepals free. Size: Length: 4.8 cm. Width: 1.3 cm. Apex: Acute. Margin: Entire. Color (when opening): Upper surface: RHS 76A (Purple). Lower surface: In between RHS 76A (Purple) to RHS 76B. (Purple) and RHS 85A (Violet). Color (fully opened): Upper surface: RHS 76A (Purple). Lower surface: In between RHS 76A (Purple) to RHS 76B. (Purple) and RHS 85A (Violet). Color fading to: RHS 85A (Violet). Texture (both surfaces): Dull, smooth.

Reproductive organs:
*Stamens.*—Quantity: 6.
*Anther.*—Shape: Dorsifixed, narrow oblong; filament curled. Length: 0.4 cm. Length of filament: 4.6 cm. Color: RHS N187A (Greyed-purple); filament colored RHS 155A (white), flushed RHS 76C (purple); base RHS 145C (Yellow-green).
*Pollen.*—Amount: Moderate. Color: RHS 12B (Yellow).
*Pistil.*—Quantity: 1. Length: 4.9 cm.
*Style.*—Length: 4.85 cm. Color: RHS 76C (Violet), lighter towards the base RHS 85B to RHS 85D.
*Stigma.*—Shape: Crested. Color: RHS 155C (White).
*Ovary color.*—RHS 144A (Yellow-green) to RHS 144B (Yellow-green), striped darker RHS 147A to RHS 147B.

Fruit and Seed Set: No fruit or seeds detected to date.

Disease and insect resistance: No particular resistance or susceptibility to diseases or insects noted to date.

COMPARISON WITH PARENTAL AND COMMERCIAL CULTIVARS

'Regal Supreme' differs from the commercial *Hosta* sp. variety 'Tom Schmid' (unpatented), by having a much wider leaf margin of color than 'Tom Schmid'.

'Regal Supreme' differs from the parent *Hosta* sp. variety 'Krossa Regal' (unpatented), in that 'Regal Supreme' has a wide leaf margin of color while 'Krossa Regal' does not have a leaf margin of color.

'Regal Supreme' differs from the commercial variety 'Forest Fire' (U.S. Plant Pat. No. 17,644) in that 'Regal Supreme' has leaves that are ovate, moderately carinate with apiculate apices, while 'Forest Fire' has broadly ovate to cordate leaves with cuspidate apices.

I claim:

1. A new and distinct cultivar of *Hosta* plant as shown and described herein.

* * * * *